US006920235B2

(12) United States Patent
Biazzi

(10) Patent No.: US 6,920,235 B2
(45) Date of Patent: Jul. 19, 2005

(54) METHOD AND INSTRUMENT FOR DETERMINING THE DISTORTION ANGLES IN TEXTILE FABRICS OR SIMILAR, WHETHER FIXED OR IN MOVEMENT

(75) Inventor: Pier Silvano Biazzi, Brescia (IT)

(73) Assignee: Ehrardt piu Leimer S.r.l., Treviolo BG (IT)

( * ) Notice: Subject to any disclaimer, the term of this patent is extended or adjusted under 35 U.S.C. 154(b) by 695 days.

(21) Appl. No.: 09/912,760

(22) Filed: Jul. 25, 2001

(65) Prior Publication Data

US 2002/0015152 A1 Feb. 7, 2002

(30) Foreign Application Priority Data

Jul. 26, 2000 (IT) .................................... BS2000A0071

(51) Int. Cl.[7] ................................................. G06K 9/00
(52) U.S. Cl. .................... 382/111; 382/280; 356/238.1; 700/130
(58) Field of Search ................................. 382/111, 108, 382/289, 280, 315; 356/238.1, 429, 432; 26/70; 73/159; 700/130, 135, 140, 143; 223/40

(56) References Cited

U.S. PATENT DOCUMENTS

| | | | | | |
|---|---|---|---|---|---|
| 3,616,132 | A | * | 10/1971 | Klingbeil et al. ........... 428/112 |
| 4,533,245 | A | * | 8/1985 | Love, III .................... 356/430 |
| 4,684,150 | A | * | 8/1987 | Specktor et al. ....... 280/86.753 |
| 4,786,177 | A | * | 11/1988 | Beckstein et al. ........... 356/429 |
| 5,172,005 | A | * | 12/1992 | Cochran et al. ........ 250/559.08 |
| 5,328,072 | A | * | 7/1994 | Ruessmann et al. .......... 226/15 |
| 5,365,084 | A | * | 11/1994 | Cochran et al. ........ 250/559.02 |
| 5,442,187 | A | * | 8/1995 | Schrauwen et al. ......... 250/548 |
| 5,506,918 | A | | 4/1996 | Ishitani |
| 5,774,177 | A | * | 6/1998 | Lane ........................... 348/88 |
| 5,790,687 | A | * | 8/1998 | McLaughlin et al. ........ 382/111 |
| 6,521,906 | B1 | * | 2/2003 | Beying et al. .......... 250/559.37 |
| 6,614,918 | B1 | * | 9/2003 | Fujita .......................... 382/112 |
| 6,621,915 | B1 | * | 9/2003 | Chen et al. .................. 382/111 |
| 6,633,383 | B1 | * | 10/2003 | Jackson et al. ............. 356/430 |
| 6,804,381 | B2 | * | 10/2004 | Pang et al. .................. 382/111 |
| 6,832,125 | B2 | * | 12/2004 | Sonnenberg et al. ........ 700/130 |
| 2001/0012381 | A1 | * | 8/2001 | Sari-Sarraf et al. ......... 382/111 |
| 2002/0009212 | A1 | * | 1/2002 | Urano et al. ................ 382/111 |
| 2002/0054694 | A1 | * | 5/2002 | Vachtsevanos et al. ..... 382/111 |
| 2003/0118229 | A1 | * | 6/2003 | Andrews et al. ............ 382/141 |

FOREIGN PATENT DOCUMENTS

EP      0 741 290 A1    11/1996

* cited by examiner

Primary Examiner—Bhavesh M. Mehta
Assistant Examiner—Barry Choobin
(74) Attorney, Agent, or Firm—Nixon & Vanderhye, PC

(57) ABSTRACT

A method for determining the angles of oblique and arched distortion in a textile fabric, with the use of at least one optical detector with axes of symmetry orienated with respect to the fabric, includes illuminating an area of the fabric with a light source. A real image of the area of the fabric is acquired in digital form, irrespectively of the orientation of the optical detector with regard to the fabric, wherein the fabric is illuminated for just the time necessary to acquire the image. The image is rotated and compensated for the orientation of the axes of the symmetry of the optical detector with regard to the fabric. Algorithms useful for the increasing the reliability of the results of subsequent processing are applied to the image, followed by a Fourier transformation. An angle of local distortion is calculated by analyzing the spectrum of the Fourier transformation and the angles of oblique and arched distortion are calculated starting from the angle of local distortion.

20 Claims, 4 Drawing Sheets

METHOD AND INSTRUMENT FOR DETERMINING THE DISTORTION ANGLES IN TEXTILE FABRICS OR SIMILAR, WHETHER FIXED OR IN MOVEMENT

FIELD OF THE INVENTION

This invention concerns the detection and measurement of certain characteristics of textile fabrics, whether fixed or in movement, and, in particular, refers to a method and an instrument for determining the distortion angles of fabrics made on the loom, meshed or the like.

BACKGROUND

The normally right-angled structure between weft and warp, created by the fabric production machinery or similar can often be altered by the machines used for subsequent phases of the processing or treatment. A similar alteration also occurs when working meshed fabrics or the like.

This deformation of the fabric is normally identifiable by the formation of an oblique distortion angle or an arched distortion angle, shown as a1 and a2, respectively, in FIG. 1. In order to bring the distortions back within acceptable standardized limits, it is necessary to use automatic machines, normally defined as "aligners", which operate according to the measurement of said angles.

Since the fabric is checked in a certain, finite number of points, depending on the number of sensors installed, the determining of these angles is carried out by means of processing the sensor data using mathematical algorithms, such as the calculation of the average values of the local deformations or the analysis of the appropriate functions calculated for the values themselves.

The number of analysis points needed to give a reliable calculation of the deformations may be obtained by installing a sufficient number of sensors, or by a smaller number of sensors, but where each is capable of analysing various points of the fabric by moving the sensor at right angles to the length of the fabric, as illustrated in FIGS. 2 and 3, respectively.

There are already various types of sensors on the market for measuring the distortion angles, made with photodiodes or other devices, which require mechanical parts that rotate or oscillate. There are also static sensors, made with CCD (charge coupled device) linear detectors, connected in various ways in order to form images over time that appear as a succession of lines.

However, all these solutions function only if there is a relative movement between the fabric and the sensor, as described, for example, in patent EP 0 741 290. Furthermore, the linear structure requires the sensor to be mounted in a pre-set direction and the measurement solution is intrinsically different in the two right-angled directions.

Therefore, generally speaking, almost all the existing systems include the use of one or more light sources in continuous operation, which requires a certain attention to energy dissipation.

SUMMARY

One aim of this invention is to propose a sensor with photosensitive elements, using CCD or CMOS technology, in which there is no longer the need to carry out periodic maintenance on the mechanical parts, typical of the existing equipment, and which functions irrespectively of its orientation towards the fabric.

Another purpose of the invention is to provide a method of detecting the distortion angles and a sensor that will allow a real image of the fabric to be obtained, just as an operator would see it, with a constant measurement solution in every direction and accurate measurements, whether the fabric is fixed or moving with respect to the sensor, without having recourse to synchronisation or other compensatory measures.

A further aim of the invention is to provide a detection method that requires just a brief light impulse, sufficient just to obtain the image, without additional waste of energy.

Yet another purpose of the invention is to propose a sensor that includes, in one single functional unit, besides the photosensitive device, all the electronic devices for storing and processing the image, the light source with its control devices, as well as the interfaces for transferring the measurements and dialoguing with the supervision and control system.

This invention is also intended for faller devices, or equipment with a similar constriction for the correction of fabric deformation etc., which includes at least one of the sensors according to the invention, held to the fixed or moving parts and, anyway, positioned with respect to the faller device itself.

Likewise, the invention can be profitably used for making checking machines and defect certification machines.

The compactness of the unit containing all the operational elements and the planning solutions adopted means that the product can be used even in environments subject to light or electromagnetic interference without having recourse to optical transmission means for the image, such as fibre optics or other.

Essentially, the method proposed for verifying the deformation of the textile fabrics or the like, is based on the 10 use of one or more sensors which analyse contemporarily, or at pre-defined moments, one or more limited areas of the fabric, combined with a supervision and control system for the sensors, which elaborates the angles of oblique and arched deformation and sees to the automatic correction.

Compared to existing solutions, therefore, this invention supplies a method and an instrument for gathering the basic information necessary for determining the distortion angles of a textile fabric or similar. On receiving a command from the supervision and control system, each area of the fabric or the like to be explored is illuminated with a light source for just the time necessary to form an image, which is memorized inside the sensor, where it is also analyzed by means of algorithms based on two-dimensional transformations such as EFT (Fast Fourier Transform), in order to determine the angle of difference to 90°.

BRIEF DESCRIPTION OF THE DRAWINGS

Further details of the invention will become clear from the following description, made with reference to the enclosed drawings, which are indicative but not binding, and in which.

DETAILED DESCRIPTION

A system for measuring the angles of local distortion a1 and/or a2 of a textile fabric 11 essentially requires at least one detector sensor 12, a transmission system 13 for the signals or information acquired, and at least one unit for processing, supervision and control 14.

According to one preferred version of the invention, the angles of local distortion are processed directly inside the sensor itself and then transmitted to the supervision and control system for commanding the correction machines as necessary.

Figure 1:
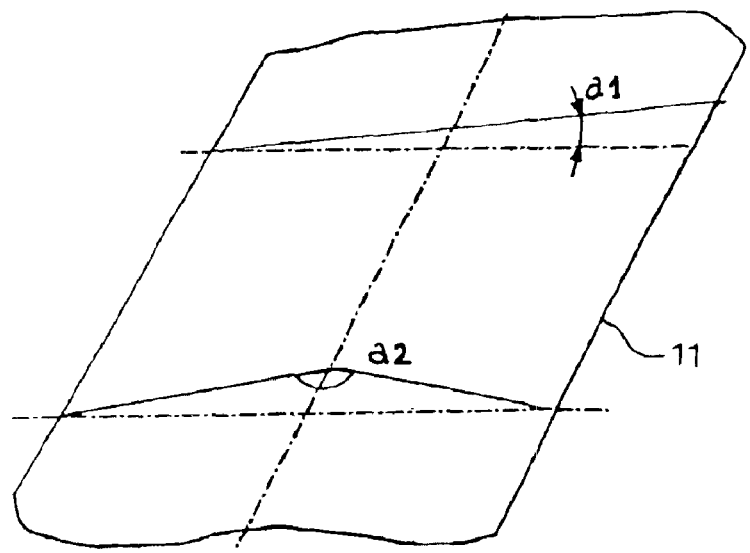
FIG. 1 shows a textile fabric on which the possible angles of oblique (a1) and arched (a2) distortion are shown.
Figure 2:
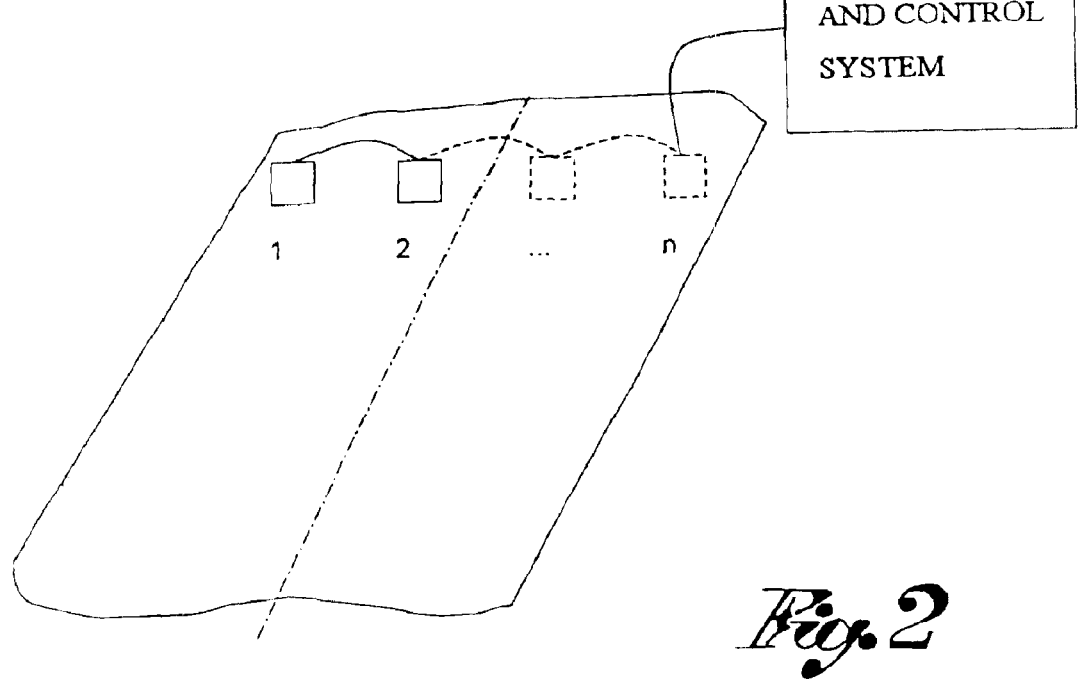
FIGS. 2 and 3 show two different layouts of the detector sensors, according to the state of the art.
Figure 3:
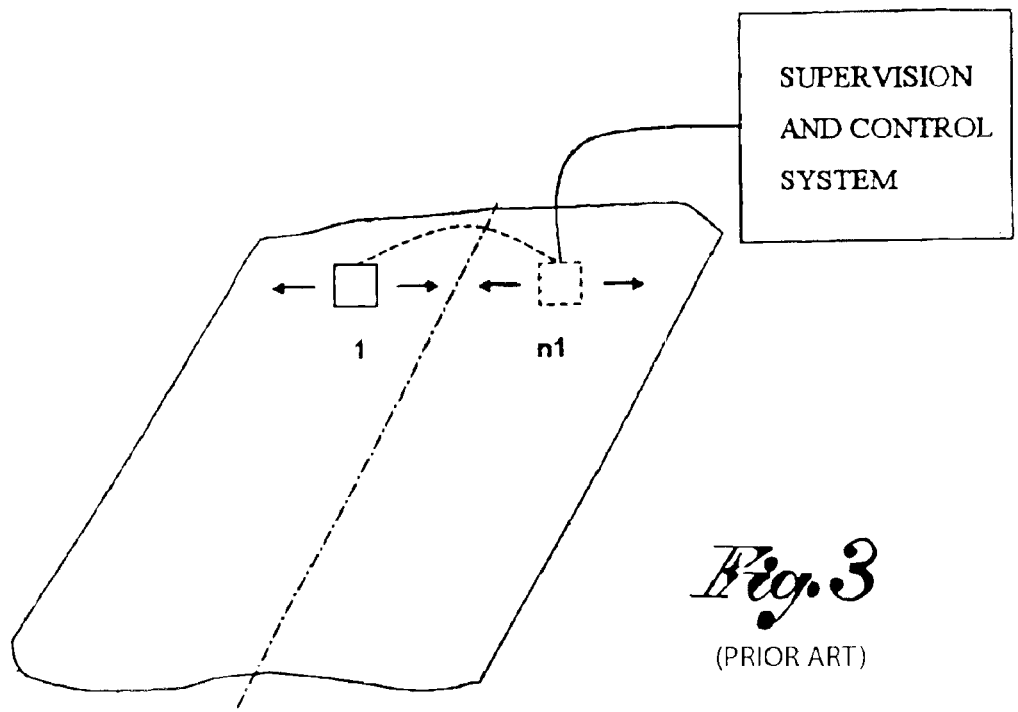
Figure 4:
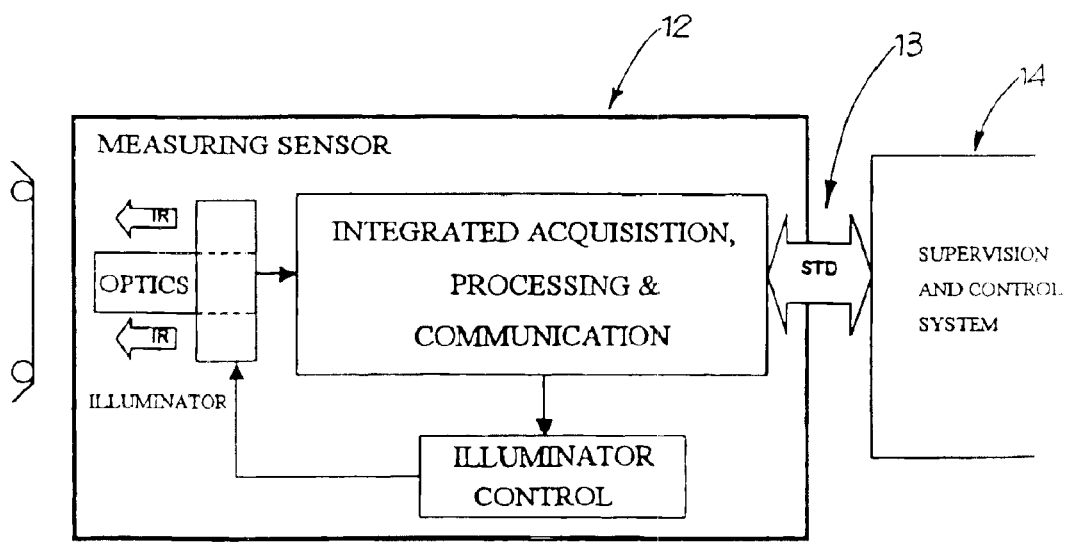
FIG. 4 shows a block diagram of the sensor according to the invention.

In fact, with reference to FIG. 4, the sensor that dialogues with the supervision and control system consists of the following functional groups:

Optics for focusing on the area of the fabric to be explored;

Impulse illuminator with solid state devices, preferably of the infra-red type;

Illuminator control circuit for commanding the duration of illumination; and

Integrated acquisition, processing and communication unit.

Figure 5:
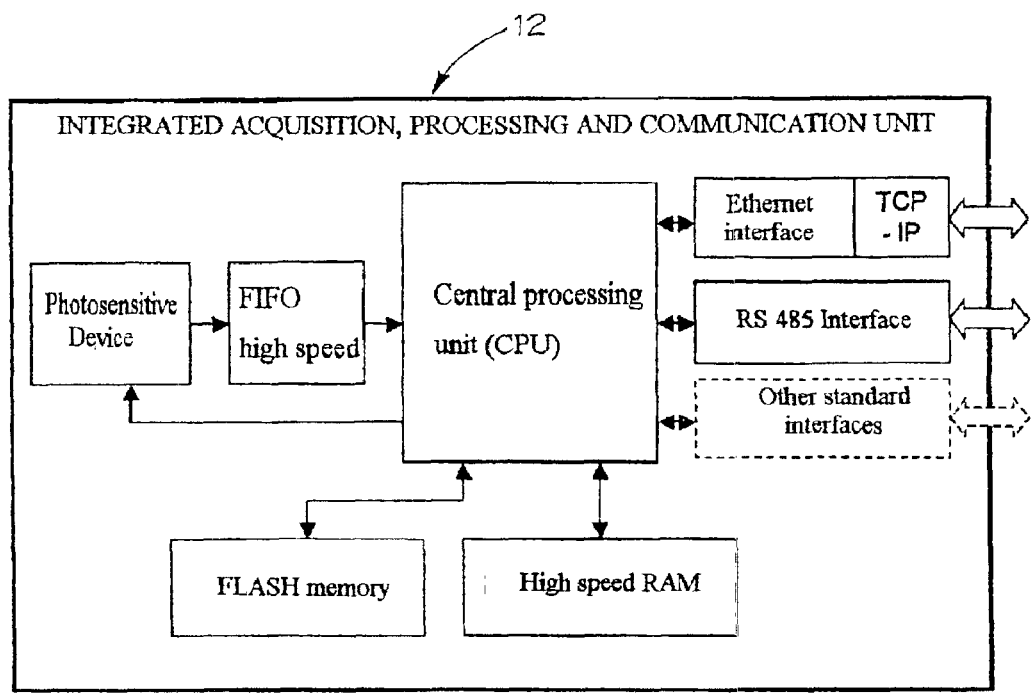
FIG. 5 shows a functional diagram of the acquisition, processing and communication block of the sensor.

In particular, the integrated acquisition, processing and communication unit consists of the following devices (FIG. 5):

Photosensitive device, CCD type or other technology, for example CMOS, in matrix;

FIFO device for direct transfer to the central processing unit of the digital image recorded by the photosensitive device;

Central processing unit responsible for:
 commanding the impulse illumination system;
 acquiring data originating from the photosensitive device;
 carrying out all the processing to obtain the angle of local deformation;
 storing all the information obtained;
 transferring the information, by means of standard interfaces, to the supervision and control system according to a predefined protocol;

FLASH memory in which there is installed the firmware which operates the unit and which stores all the data regarding the sensor functioning;

RAM memory for dynamic storing of the service data;

Ethernet interface, operating with the TCP-IP protocol;

Serial interface half duplex RS 485;

Any other interface of another type, for example, RS 422 or other.

The use of a photosensitive matrix device means that an asynchronous record can be made of the fabric image, for example, when requested by the supervision and control system. With such a matrix device, illumination of the area of fabric to be explored is reduced, in fact, to a brief impulse which is just sufficient to obtain the image, corresponding, practically, to a photograph.

Furthermore, the asynchronous image acquisition makes it possible to analyse the distortion angles even of a fabric which is fixed or at an angle with respect to the sensor.

The supervision and control system is made with a structure based on personal computer which, apart from determining the values of the angles of oblique and arched deformation on the basis of the angles of local deformation provided by the sensors, also provides the functions of user interface and the control of any processing machines.

Figure 6:
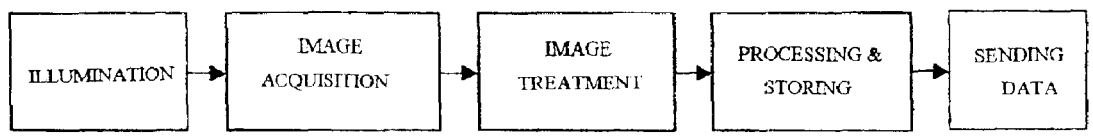
FIG. 6 shows the flow diagram of the various detection phases of the distortion angles of the fabric, according to the method of the invention.

The procedure for determining the angles of local deformation consists of the following steps (FIG. 6):

impulse illumination of an area of the fabric with a light source, preferably solid state with infra-red emission;

acquisition, in digital form, of the real image of the area of fabric under study, irrespectively of the orientation of the optical detector with regard to the fabric, with illumination of the fabric itself for a period just long enough to acquire the image;

treatment of the image, that is, compensation of the orientation of the axes of symmetry of the optical detector with respect to the fabric and application of the algorithms useful for increasing the reliability of the results of subsequent processing;

data processing, that is, application of the two-dimensional Fourier transformation to the recorded image and determination of the angle of local deformation by means of analysis of the two-dimensional spectrum obtained;

transmitting the value of the local distortion angle and messages about the operating state of the sensor to the supervision and control system.

Figure 7:
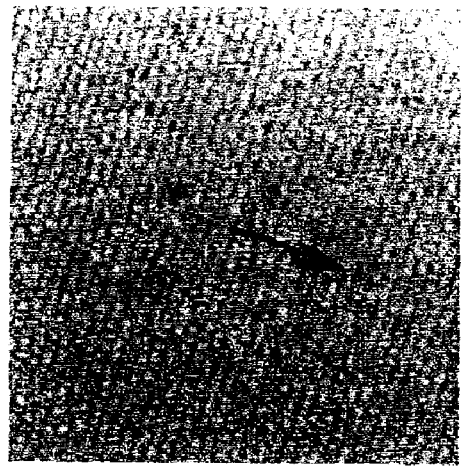
FIG. 7 shows an image of the fabric when fixed, or in movement, as it is recorded by the sensor and visualized on the user interface of the supervision and control system.

An example of the digital image acquired by the sensor and visualized by the supervision and control system is illustrated in FIG. 7, in which there can be seen the image as it would appear to the operator who was observing the area under study.

Figure 8:
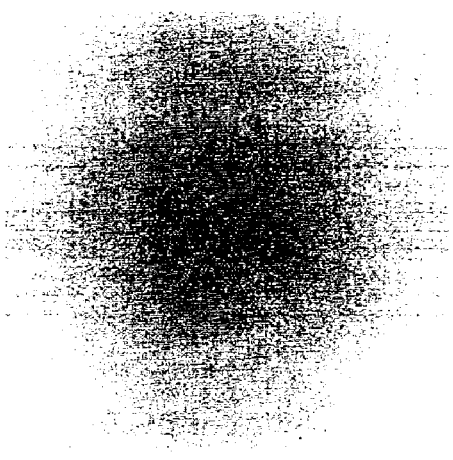
FIG. 8 shows a two-dimensional frequency spectrum as it is elaborated by the sensor and visualized on the user interface of the supervision and control system.

Applying the Fourier transformation to this image, we obtain the two-dimensional spectrum represented in FIG. 8 as it could be acquired and visualized by the supervision and control system. The co-ordinates of these points constitute the basic data for determining the angle of local deformation.

What is claimed is:

1. A method for determining angles of oblique and arched distortion of a textile fabric, with the use of at least one optical detector with axes of symmetry orientated with respect to the fabric, the method comprising:

illuminating an area of the fabric with a light source;

acquiring, in digital form, a real image of the area of the fabric, irrespectively of the orientation of the optical detector with respect to the fabric, wherein the fabric is illuminated for just the time necessary to acquire the image;

rotating the image and compensating for the orientation of the axes of symmetry of the optical detector with respect to the fabric;

applying to the image algorithms useful for increasing the reliability of the results of subsequent processing;

applying a two-dimensional Fourier transformation to the image;

calculating an angle of local distortion by analyzing the spectrum of the Fourier transformation; and calculating the angles of oblique and arched distortion, starting from the angle of local distortion.

2. The method according to claim 1, wherein the value of the local angle is generated only on a request from a central supervision and control system.

3. The method according to claim 1, wherein the illuminating of the fabric is carried out with single impulses and the acquiring of the images is synchronized with the impulses.

4. The method according to claim 1, wherein the fabric is fixed.

5. The method according to claim 1, wherein the fabric is moving.

6. A sensor for determining the angles of oblique and arched distortion of a fabric according to the method of claim 1, the sensor including within a single functional unit:
   focusing optics;
   an illuminator control circuit for controlling the duration of the illuminating; and
   an integrated acquisition, processing and communication unit.

7. The sensor according to claim 6, wherein the integrated acquisition, processing and communication unit includes a static matrix photosensitive device.

8. A faller device for treatment of textile fabric, the faller device comprising actuators for controlling correction of distortion angles, at least one sensor according to claim 6 for detecting local distortions, and a supervision and control system for acquiring and processing the values of the local distortions, and for controlling the actuators of the faller machine.

9. A machine for controlling and certifying defects in textile fabrics, the machine being configured to implement the method of claim 1.

10. The method according to claim 2, wherein the illuminating of the fabric is carried out with single impulses and the acquiring of the images is synchronized with the impulses.

11. The method according to claim 2, wherein the fabric is moving.

12. The method according to claim 3, wherein the fabric is moving.

13. A faller device for treatment of textile fabric, the faller device comprising actuators for controlling correction of the distortion angles, at least one sensor according to claim 7 for detecting local distortions, and a supervision and control system for acquiring and processing the values of the local distortions, and for controlling the actuators of the faller machine.

14. A machine for controlling and certifying defects in textile fabrics, the machine being configured to implement method of claim 2.

15. A machine for controlling and certifying defects in textile fabrics, the machine being configured to implement the method of claim 3.

16. A machine for controlling and certifying defects in textile fabrics, the machine being configured to implement the method of claim 4.

17. A machine for controlling and certifying defects in textile fabrics, the machine being configured to implement the method of claim 5.

18. A machine for controlling and certifying defects in textile fabrics, the machine being configured to implement the method of claim 6.

19. A machine for controlling and certifying defects in textile fabrics, the machine being configured to implement the method of claim 7.

20. A machine for controlling and certifying defects in textile fabrics, the machine being configured to implement the method of claim 8.

* * * * *